US007205440B2

United States Patent
Wenzl et al.

(10) Patent No.: US 7,205,440 B2
(45) Date of Patent: Apr. 17, 2007

(54) METHOD OF PRODUCING AMINES

(75) Inventors: Peter Wenzl, Köln (DE); Friedrich Dürrholz, Remscheid (DE); Herbert V. Diehl, Leverkusen (DE)

(73) Assignee: Lanxess Deutschland GmbH, Leverkusen (DE)

( * ) Notice: Subject to any disclaimer, the term of this patent is extended or adjusted under 35 U.S.C. 154(b) by 284 days.

(21) Appl. No.: 10/499,876

(22) PCT Filed: Dec. 17, 2002

(86) PCT No.: PCT/EP02/14388

§ 371 (c)(1),
(2), (4) Date: Jan. 4, 2005

(87) PCT Pub. No.: WO03/051817

PCT Pub. Date: Jun. 26, 2003

(65) Prior Publication Data

US 2005/0113582 A1    May 26, 2005

(30) Foreign Application Priority Data

Dec. 19, 2001   (DE) ............................. 101 62 684

(51) Int. Cl.
*C07C 209/58* (2006.01)
(52) U.S. Cl. ..................................... 564/414
(58) Field of Classification Search ................ 564/414
See application file for complete search history.

(56) References Cited

U.S. PATENT DOCUMENTS

| 4,590,292 | A | 5/1986 | Blackwell et al. ........... 560/124 |
| 5,001,124 | A | 3/1991 | Patterson et al. ........ 514/236.8 |
| 5,032,687 | A | 7/1991 | Diehl et al. ..................... 564/1 |
| 5,034,410 | A | 7/1991 | Sjogren et al. ............. 514/516 |
| 5,068,428 | A | 11/1991 | Diehl et al. .................. 564/134 |
| 5,130,441 | A | 7/1992 | Gluchowski ................. 548/351 |
| 5,410,082 | A | 4/1995 | Pfirmann ..................... 564/414 |
| 5,698,711 | A | 12/1997 | Palfreyman .................. 549/66 |
| 5,935,978 | A | 8/1999 | Fenton et al. ............... 514/352 |
| 6,255,326 | B1 | 7/2001 | Ashton et al. .............. 514/352 |

FOREIGN PATENT DOCUMENTS

| EP | 275 971 | 7/1988 |
| GB | 1257097 | 12/1971 |
| JP | 61-271255 | 1/1986 |
| WO | 91/15464 | 10/1991 |

OTHER PUBLICATIONS

Org. React. 3, 277-282 (1946), Hauser et al The Hoffman Reaction Aromatic and Heterocyclic Amides.
J. Am. Chem. Soc., 59, pp. 121-125 (1931), Hauser et al "The Removal of HX from Organic Compounds by Means of Bases. III. The Rates of Removal of Hydrogen Bromide from Substituted N-Bromobenzamides and their Relative Ease of Rearrangement in the Presence of Alkali. the Hofmann Rearrangement".
J. Am. Chem. Soc., vol. 60, 2308-2311 (1937), Crenshaw, Cope, Finkelstein and Rogan The Dioxanates of the Mercuric Halides.
J. Am. Chem. Soc., vol. 61, pp. 618-629 (1939), Bright and Hauser; "The influence of Substituents on the Rates of Composition of the Potassium Salts of Dihyroxamic Acids. The Lossen Rearrangement".
J.X. Wang et al, J. Chem. Research (S) 1986, pp. 456-457 "Phase-tansfer-catalysed Hydration of Nitriles to Amides induced by Pentacarbonylmanganese Bromide".
D.E. Welch et al, J. Med. Chem (12), 1969, pp. 299-303 "α,60 ,α-Trifluorotoluamides as Anti-coccidial Agents".

*Primary Examiner*—Taofiq Solola
(74) *Attorney, Agent, or Firm*—Michael A. Miller

(57) ABSTRACT

The invention relates to a special two-step method for producing amines on the basis of amides by reacting them with halides or hypohalites in an aqueous solution in a Hofmann degradation reaction. The amide is reacted in an alkaline solution and/or suspension with halides or hypohalites and the reaction mixture obtained in step 1 is added to an aqueous alkaline solution having a temperature of at least 40° C.

16 Claims, No Drawings

METHOD OF PRODUCING AMINES

The present invention relates to a novel process for preparing amines by means of specifically reacting appropriate carboxamides with hypohalites or halogens in alkaline aqueous solution.

Amines, in particular aromatic amines, are important precursors for producing phytoprotective agents, pharmaceuticals and liquid crystals. Examples of aromatic amines of interest are 2,6-dihaloanilines, in particular 2,6-difluoroaniline and 2,6-dichloroaniline, and also 2,3,5,6-tetrafluoroanalines. 4-Trifluoromethylaniline, or aliphatic amines, such as cyclopropylamine, are also of importance.

2,6-Difluoroaniline is used, for example, as an intermediate for producing pharmaceuticals (EP-A-0 497 564 and WO-A-91/15464) and liquid crystals for use in displays. 2,6-Dichloroaniline can also be used as a building block for synthesizing highly active pharmaceuticals (EP-A-0 497 564 and U.S. Pat. No. 5,130,441). Aside from other applications, 4-trifluoromethylaniline is used for producing anthelmintics (U.S. Pat. No. 5,034,410) and antiinflammatory and immunomodulating agents (U.S. Pat. No. 5,001,124). The area of application which is currently the most important in the case of cyclopropylamine is that of preparing fluorinated quinolonecarboxylic acids (DE-A-34 20 789, EP-A-275 971), which have gained great importance as antibacterial agents.

The use of Hofmann degradation to prepare amines from the corresponding carboxamides is known in principle. However, the synthesis frequently only proceeds with moderate yields and selectivities. Side reactions occur, in some cases on a substantial scale, under the drastic reaction conditions, with examples of these side reactions being hydrolysis of the amide, ring chlorination and oxidative degradation, particularly as a result of oxidation at the nitrogen, with this oxidation being caused by the oxidative effect, which appears at the high reaction temperatures, of the hypochlorites or of the N-chloro compounds which are formed. In some cases, it is necessary to add expensive or toxic auxiliary substances such as phase transfer catalysts (JP 61 271255). As a consequence of the negative factors, it is uneconomical to use this route of synthesis for preparing many amines.

In the case of 2,6-disubstituted aromatic amides, the addition of hydroxide to the intermediate isocyanate during the Hofmann degradation is unfavorable for steric reasons, particularly when relatively large substituents are present (Org. React. 3, 277–282 (1946)). Such reactions are therefore scarcely known, either.

Furthermore, electrophilic substituents facilitate the undesirable hydrolysis of the amide bond in the starting compound to give the carboxylate, with this simultaneously retarding the rearrangement.

While the rearrangement is favored in the case of electron-donating substituents, such as alkoxy or hydroxyl groups, the ring chlorination is also disadvantageously accelerated (e.g. Haufer et al., J. Am. Chem. Soc. 59, 121 (1937) ibid. 60, 2308 (1937), ibid. 61, 618 (1939)).

It is furthermore known that, while increasing the temperature favors the rearrangement within the context of the Hofmann degradation as opposed to the undesirable hydrolysis of the amide, it also results in the strongly oxidizing and halogenating character of the reagent becoming noticeable once again. However, this is not particularly advantageous, and in fact undesirable, particularly in the case of oxidation-sensitive amines, in particular in the case of aromatic amines.

EP-A-0 367 010 discloses a process for using Hofmann degradation to prepare cyclopropylamine from cyclopropanecarboxamide. In this connection, it is crucial that the cyclopropanecarboxylic acid is used in the form of an aqueous solution instead of in the form of a suspension.

In the case of aliphatic and cycloaliphatic amides, the formation of alkyl-acyl ureas occurs as the most frequent side reaction.

EP-A-0 628 536 discloses a special process for preparing amines by Hofmann degradation of the corresponding amides. This process is characterized in that amides are reacted, in aqueous-alkaline solutions and/or suspensions, with halogens or hypohalites and the reaction products are converted into the amines by hydrolysis or hydrogenation or using reductive methods. The crucial point is that the reaction is carried out in the presence of alcohols. In this connection, the halogen, or a solution of the hypohalite, is metered, in a one-pot reaction, into the initially introduced aqueous alkaline solution of amide and alcohol. After the metering in has been concluded, steam is conducted into the reaction mixture and the desired amine is distilled off. For a variety of aromatic amines, the yields are in the range between 51 and 92% and are consequently not universally satisfactory.

Because of the great need, as has been described, for amines and, in particular, substituted aromatic amines, the object of the invention was to provide a novel process for preparing amines, which process does not suffer from the above-described disadvantages, uses readily available starting materials, provides the desired compounds in high yields and, furthermore, can be implemented industrially without any great input as regards safety engineering.

This object is achieved by means of a process for preparing amines, characterized in that 1. an amide is reacted, in an aqueous alkaline solution and/or suspension, with halogens or hypohalites, and
2. the reaction mixture obtained in step 1 is then added to another aqueous alkaline solution whose temperature is at least 40° C.

This novel process can be used, surprisingly, to convert a very wide variety of amides into the corresponding amines with high yields.

Thus, $(C_1–C_{10})$-alkylamides can be used very successfully, with it being possible for the alkyl radical in turn to be substituted by from one to four $(C_1–C_4)$-alkyl groups, $(C_1–C_4)$-alkoxy groups, fluorine, chlorine or bromine atoms, $NO_2$, CN, $CF_3$, $CHF_2$ or $(C_1–C_4)$-alkoxycarbonyl groups, or benzyloxy groups whose phenyl radical can in turn carry from one to three $(C_1–C_4)$-alkyl groups, $(C_1–C_4)$-alkoxy groups, fluorine, chlorine or bromine atoms, for $NO_2$, CN, $CF_3$, $CHF_2$ or $(C_1–C_4)$-alkoxycarbonyl groups.

The process according to the invention has also proved to be of value for preparing aromatic amines using aromatic amides, with the aromatic radical being phenyl, naphthyl, biphenyl or heteroaryl, preferably pyridine, thiophene or pyrrole, and with it being possible for the aromatic radical to be substituted by one or more chlorine, fluorine or bromine atoms, or $CF_3$, $CHF_2$, $NO_2$ CN, carboxyl, $(C_1–C_4)$-alkoxycarbonyl, $(C_1–C_4)$-alkyl or $(C_1–C_4)$-alkoxy groups.

The process according to the invention is particularly suitable for preparing amines of the general formula (I)

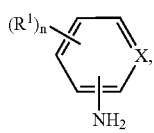

where
X can be carbon or nitrogen,
n is 0, 1, 2, 3, 4 or 5, if X is carbon, or
n is 0, 1, 2, 3 or 4 if X is nitrogen,
$R^1$ is identical or different and is halogen, preferably fluorine, chlorine, bromine or iodine, $CF_3$, $(C_1-C_4)$-alkyl, $(C_1-C_4)$-alkoxy, $NO_2$ or CN.

In these cases, compounds of the general formula (II)

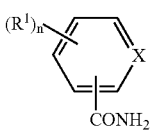

in which X, n and $R^1$ have the meanings mentioned for the general formula (I), are used as starting compounds.

The compounds which are to be employed in the process according to the invention are either obtainable commercially or can be prepared by the skilled person using methods of the prior art.

2,6-difluorobenzamide, which is the starting material for 2,6-difluoroaniline, is obtained from 2,6-difluorobenzonitrile using methods which are well known in the literature (J. March, Advanced Organic Chemistry (1985), 788). It is possible, for example, to react 2,6-difluorobenzonitrile with hydrogen peroxide in an aqueous-alkaline medium. 2,6-Dichlorobenzamide is prepared from 2,6-dichlorobenzonitrile in an analogous manner. 4-Trifluoromethylbenzamide can be prepared, for example, from 4-trifluoromethylbenzonitrile (J. X. Wang et al., J. Chem. Res. Synop., (12), 456–457) or from 4-trifluoromethylbenzoic acid (D. E. Walch et al., J. Med. Chem. 12 (1969), 299–303). Several industrially feasible routes exist for preparing cyclopropanecarboxamide (EP-A-0 365 970 and DE-A 30 26 094).

2,3,5,6-Tetrafluorobenzamide can be obtained, for example, by converting 2,3,5,6-tetrafluorobenzoic acid into 2,3,5,6-tetrafluorobenzoyl chloride and then amidating.

It is also possible to prepare the 2,3,5,6-tetrafluorobenzamide from 2,3,5,6-tetrafluorobenzonitrile in a manner which is known per se.

Particular preference is given to the preparation, according to the invention, of 2,3,5-6-tetrafluoroaniline from 2,3,5,6-tetrafluorobenzamide and to the preparation of 3-amino-6-trifluoromethylpyridine from 6-trifluoromethylnicotinamide.

In step 1 of the process according to the invention, the carboxamide is initially reacted with halogens or hypohalites in an aqueous alkaline solution and/or suspension.

Generally speaking, the procedure in this step 1 is that
a) an aqueous alkaline solution is metered into an aqueous solution and/or suspension of the appropriate amide, and
b) either the halogen or the aqueous hypohalite solution is metered into this solution and/or suspension.

An aqueous solution of alkali metal or alkaline earth metal compounds, which compounds have an alkaline effect, can be used as the aqueous alkaline solution mentioned under a). These compounds can, for example, be hydroxides, carbonates, hydrogen carbonates, phosphates, hydrogen phosphates, dihydrogen phosphates or oxides, or similar compounds or mixtures thereof. Preference is given to the corresponding alkali metal compounds, in particular sodium hydroxide, potassium hydroxide, sodium carbonate and/or potassium carbonate. The alkali metal or alkaline earth metal compounds having an alkaline effect are used in quantities of from 0.9 to 6 mol, preferably of from 0.95 to 3 mol and, particularly preferably of from 0.98 to 2 mol, based on 1 mol of amide to be degraded. The concentration of the aqueous alkaline solution is not critical and can be optimized in dependence on the amide which is used.

The halogens employed can, for example, be chlorine or bromine, while the hypohalites employed can be sodium hypochlorite or sodium hypobromite. Under b), bromine is added dropwise in the form of a liquid whereas chlorine is conducted in in the form of a gas.

In this connection, using hypohalite solutions (bleaching solutions) is equivalent to metering elemental halogen into the aqueous alkaline solutions and/or suspensions of the amide. In order to describe the reaction conditions, it is sufficient to specify the quantity of halogen employed since hypohalite solutions are formed in situ when the halogen makes contact with the aqueous solutions having an alkaline effect which are employed. Chlorine or bromine are therefore used in quantities of from 1 to 5 mol, in particular of from 1.01 to 2 mol, particularly preferably of from 1.02 to 1.2 mol, in each case based on 1 mol of amide to be degraded. Preference is given to using chlorine because it is more readily available industrially.

If bleaching solutions, that is aqueous hypohalite solutions, are metered in, an approach which, on a laboratory scale, generally has advantages in regard to manipulation when compared with using elemental halogen, use is then made of solutions which have a content of active chlorine of from about 30 to about 250 g per kg of solution, preferably of from about 100 to about 200 g of active chlorine per kg of solution, or of from about 60 to about 550 g of active bromine per kg of solution, preferably of from about 200 to about 350 g per kg of solution. These solutions can be obtained by metering the appropriate quantities of chlorine or bromine into aqueous solutions having an alkaline effect.

During the addition of the halogen or of the hypohalite solution, the temperature of the reaction mixture is maintained in the range from −10° C. to 20° C., preferably of from 0 to 15° C., particularly of from 0 to 10° C. The halogen or the hypohalite solution is usually added under normal pressure.

The time taken for the metering in is chosen in dependence on the size of the mixture such that the temperature of the reaction mixture is in the abovementioned range.

If the halogen or hypohalite is employed in a molar ratio of >1 based on the amide, it is then particularly advantageous, after step 1, to destroy the excess halogen or hypohalite by adding a reducing agent, preferably a bisulfite solution or $SO_2$, and thereby remove it from the reaction system. It has proved to be particularly worthwhile not to add the reducing agent immediately after the metering-in of the halogen/hypohalite has been completed but, instead, to add it more than 2 hours, preferably at least 2.5 hours and in particular at least 3 hours, after the addition of the halogen or the hypohalite has been completed. The temperature during this period before adding the reducing agent is in the same range as for the preceding reaction, i.e. in the range of from −10° C. to +20° C., preferably of from 0° C. to 15° C. and in particular of from 0 to 10° C. This once again markedly increases the yield of the overall process. If a large excess of halogen or hypohalite is used, i.e. in the region of 1.5–2 mol based on 1 mol of amide to be converted, it is then also possible, where appropriate, to decrease the specified secondary reaction time.

At the end of step 1, there then exists a solution of the N-haloamide salt containing the corresponding alkali metal cation or alkaline earth metal cation as the counterion.

In step 2 of the process according to the invention, the procedure is such that the solution from step 1, i.e. the solution of the N-haloamide salt, is added to another aqueous alkaline solution whose temperature is at least 40° C.

In principle, it is possible to use the same alkaline solutions as were employed in step 1 as the aqueous alkaline solution which is to be introduced initially.

It is particularly advantageous if the reaction solution obtained in step 1, i.e. the solution of the N-haloamide salt, whose temperature is usually in the range from −10 to 20° C., is metered continuously, and preferably slowly, into the aqueous alkaline solution. It is less advantageous for this reaction solution from step 1 to have any higher temperatures since this can lead to problems with regard to safety engineering and to an increased formation of byproducts. A period of at least 3 hours, preferably at least 5 hours and, in the case of mixtures having relatively large volumes, in particular a period of from 6 to 8 hours, has been found to be advantageous for the metering-in. If the N-haloamide salt is metered in more rapidly, this then results in a markedly lower product yield.

During this metering-in, the temperature of the reaction mixture rises and is maintained in the range of from 40 to 110° C., preferably in the range of from 50 to 110° C., particularly preferably in the range of from 90 to 109° C., and in particular in the range of 100–108° C. When setting the temperature, care must be taken to ensure that the rate of metering in at this temperature is not higher than the rate of the Hofman rearrangement in step 2. If this point is not observed, this then leads, particularly in the case of mixtures which are of relatively large volume, to a situation which is critical from the point of view of safety engineering.

While step 2 of the process according to the invention is usually carried out under normal pressure, it can also be carried out under a reduced pressure of up to approximately 80 mbar.

It is advantageous for the process according to the invention to remove the amine which is formed in step 2 from the reaction mixture directly and continuously. This is usually effected by distilling off. If the product is not separated off directly and continuously, this can then result, in the case of oxidation-sensitive amines, in the product yield and/or product quality being lower.

The desired product can be obtained, or subjected to further purification, using the isolation and purification methods which are customary and which will depend on the substance properties of the product (physical state and solution behavior). A simple phase separation, which can be improved by adding solvents, is particularly suitable in the case of liquid products which are not miscible with water. Many of the amines which are to be prepared are volatile with steam, which means that steam distillation constitutes a method for separating the product from the reaction mixture which is both mild and technically easy to implement. Solid products can be isolated by filtration or extraction and then purified by crystallization. Both distillation and chromatography can be used for purifying liquid and solid products; liquid products are as a rule fractionated.

The distinguishing feature of the process according to the invention is that it is conducted simply in two steps. Excellent conversions and purities, and consequently yields of amine, are obtained simply using water as solvent, i.e. without any addition of phase transfer catalysts or alcohols. The fact that it is not necessary, in the conversion according to the invention, to add alcohols or other organic solvents results in advantages in regard to safety engineering, particularly when the mixtures are of relatively large volume. Unwanted byproducts and secondary components, such as 4-chloro-2,3,5,6-tetrafluoroaniline, 2,3,4,6-tetrafluoroaniline and 2,3,4,5-tetrafluoroaniline when preparing 2,3,5,6-tetrafluoroanaline, are either not found at all or only found in extremely small quantities.

EXAMPLES 1–7

Preparing 2,3,5,6-tetrafluoroaniline from 2,3,5,6-tetrafluorobenzamide

Step 1a)

96.6 g (0.5 mol; 1 equiv.) of 2,3,5,6-tetrafluorobenzamide are added to 500 ml of water while stirring. The suspension is then cooled down to a temperature which is in the range from 0 to 10° C. While stirring, 60 ml (0.98 equiv.) of a 45% solution of sodium hydroxide are metered in such that the temperature is maintained in the range of from 0 to 10° C.

Step 1b)

The quantity of a 14% solution of sodium hypochlorite which is specified in Table 1 is then added dropwise, while stirring, with the temperature being kept in the range of from 0 to 10° C. over the whole of the time taken for the dropwise addition. After the addition of the sodium hypochlorite solution has been completed, the 2,3,5,6-tetrafluorobenzamide is completely dissolved, and the solution is kept at a temperature in the range of from 0 to 10° C. for the period specified in Table 1 to allow the secondary reaction to take place. The quantity of a 10% (or 20% in the case of experiment 8) solution of sodium bisulfite specified in Table 1 is then added, while stirring, at a temperature of from 5 to 10° C.

Step 2)

500 ml of water and 89 g (61 ml) of a 45% solution of sodium hydroxide are then initially introduced, with this solution being heated to boiling while being stirred. The solution of the sodium salt of the N-chloroamide, which was obtained in step 1) and whose temperature is in the range of from 0 to 10° C., is metered in continuously over the period specified in Table 1.

In experiments 2–6, water and the resulting product 2,3,5,6-tetrafluoroaniline are distilled off directly and continuously, during the metering-in, into a distillation receiver. The product solidifies as the lower phase. The water is separated off from this solidified organic phase.

In experiment 1, water and product are not distilled off until the metering-in has come to an end.

In experiment 7, water and product are not distilled off until twelve hours after the metering-in has come to an end, with the reaction mixture remaining at 20° C. and at rest during these twelve hours.

The desired product is obtained as a slightly pink liquid. The yield, based on the quantity of 2,3,5,6-tetrafluorobenzamide employed, which was obtained in the respective experiments and determined by means of GC, and also the percentage content of the byproduct 4-chloro-2,3,5,6-tetrafluoroaniline (4-Cl-TEFA), are given in Table 1.

TABLE 1

|  | Example | | | | | | |
|---|---|---|---|---|---|---|---|
|  | 1 | 2 | 3 | 4 | 5 | 6 | 7 |
| Bleaching solution (g/ml/mol) | 272 | 272 | 272 | 272 | 272 | 272 | 272 |
|  | 226 | 226 | 226 | 226 | 226 | 249 | 226 |
|  | 0.51 | 0.51 | 0.51 | 0.51 | 0.51 | 0.56 | 0.51 |
| Duration of the secondary reaction in step 1 b (h) | 1 | 4.5 | 6 | 4 | 2 | 17 | 16 |
| Sodium bisulfite solution (g) | 11.9 | 32.7 | 16.7 | 24 | 38.8 | 142.2 | 6.7 |
| Duration of the metering-in in step 2 (h) | 4.5 | 2 | 6 | 6 | 6 | 6 | 5.75 |
| 4-Cl-TEFA (%) | 0.06 | 0.06 | 0.02 | 0.08 | 0.03 | 0.01 | 0.12 |
| Yield (%) | 81.1 | 79.4 | 90.8 | 92.1 | 82.5 | 93.1 | 89.8 |

The invention claimed is:

1. A process for preparing amines, characterized in that
   1) an amide is reacted with halogens or hypohalites in an aqueous alkaline solution and/or suspension, and
   2) the reaction mixture obtained in step 1 is then added to another aqueous alkaline solution whose temperature is at least 40° C.

2. The process as claimed in claim 1, characterized in that, in step 1,
   a) an aqueous alkaline solution is metered in to an aqueous solution and/or suspension of the appropriate amide, and
   b) either the halogen or the aqueous hypohalite solution is metered in to this solution and/or suspension.

3. The process as claimed in claim 1, characterized in that use is made of $(C_1–C_{10})$-alkylamides, where the alkyl radical can, in turn be substituted by from one to four $(C_1–C_4)$-alkyl groups, $(C_1–C_4)$-alkoxy groups, fluorine, chlorine or bromine atoms, $NO_2$, CN, $CF_3$, or $(C_1–C_4)$-alkoxycarbonyl groups, or benzyloxy groups whose phenyl radical can in turn carry from one to three $(C_1–C_4)$-alkyl groups, $(C_1–C_4)$-alkoxy groups, fluorine, chlorine or bromine atoms, or $NO_2$, CN, $CF_3$, $CHF_2$ or $(C_1–C_4)$-alkoxycarbonyl groups.

4. The process as claimed in claim 1, characterized in that use is made of aromatic amides, where the aromatic radical is phenyl, naphthyl, biphenyl or heteroaryl, preferably pyridine, thiophene or pyrrole, and the aromatic radical can be substituted by one or more chlorine, fluorine or bromine atoms, or $CF_3$, $CHF_2$, $NO_2$ CN, carboxyl, $(C_1–C_4)$-alkoxycarbonyl, $(C_1–C_4)$-alkyl or $(C_1–C_4)$-alkoxy groups.

5. The process as claimed in claim 1, for preparing amines of the general formula (I)

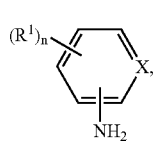

(I)

where

X can be carbon or nitrogen, n is 0, 1, 2, 3, 4 or 5 if X is carbon, or n is 0, 1, 2, 3 or 4 if X is nitrogen, $R^1$ is identical or different and is halogen, preferably fluorine, chlorine, bromine or iodine, $CF_3$, $(C_1–C_4)$-alkyl, $(C_1–C_4)$-alkoxy, $NO_2$ or CN, from compounds of the general formula (II)

(II)

in which X, n and $R^1$ have the meanings mentioned for the general formula (I).

6. The process as claimed in claim 5 for preparing 2,3,5,6-tetrafluoroaniline from 2,3,5,6-tetrafluorobenzamide or for preparing 3-amino-6-trifluoromethylpyridine from 6-trifluoromethylnicotinamide.

7. The process as claimed in claim 1, characterized in that the halogens employed are chlorine or bromine and the hypohalites employed are sodium hypochlorite or sodium hypobromite.

8. The process as claimed in claim 1, characterized in that chlorine or bromine is used in quantities of from 1 to 5 mol, in particular of from 1.01 to 2 mol, particularly preferably of from 1.02 to 1.2 mol, in each case based on 1 mol of amide.

9. The process as claimed in claim 1, characterized in that use is made of hypohalite solutions which have a content of active chlorine of from about 30 to about 250 g per kg of solution, preferably of from about 100 to about 200 g of active chlorine per kg of solution or of from about 60 to about 550 g of active bromine per kg of solution, preferably of from about 200 to about 350 g per kg of solution.

10. The process as claimed in claim 1, characterized in that the temperature of the reaction mixture is kept in the range of from –10° C. to 20° C., preferably of from 0 to 15° C., in particular of from 0 to 10° C., during the addition of the halogen or of the hypohalite solution in step 1.

11. The process as claimed in claim 1, characterized in that the halogen or hypohalite is employed in a molar ratio of >1 based on the amide and, after step 1, excess halogen or hypohalite is destroyed, and removed from the reaction system, by adding a reducing agent, preferably a bisulfite solution or $SO_2$.

12. The process as claimed in claim 11, characterized in that the reducing agent is added more than 2 hours, preferably at least 2.5 hours and in particular at least 3 hours after the addition of the halogen/hypohalite has come to an end and, during this period before adding the reducing agent, the temperature is in the range of from −10° C. to +20° C., preferably of from 0° C. to 15° C. and in particular of from 0 to 10° C.

13. The process as claimed in claim 1, characterized in that, in step 2, the reaction solution obtained from step 1 is metered continuously into the aqueous alkaline solution, with the temperature of the reaction solution obtained from step 1 being in the range of from −10 to 20° C., preferably of from 0 to 15° C., in particular of from 0 to 10° C.

14. The process as claimed in claim 1, characterized in that the temperature of the reaction mixture in step 2 is in the range of from 40 to 110° C., preferably in the range of from 50 to 110° C., particularly preferably in the range of from 90 to 109° C., and particularly in the range of 100–108° C.

15. The process as claimed in claim 1, characterized in that the reaction solution obtained in step 1 is metered in over a period of at least 3 hours and preferably at least 5 hours, in particular over a period of from 6 to 8 hours.

16. The process as claimed in claim 1, characterized in that the amine formed in step 2 is removed directly and continuously from the reaction mixture while the reaction solution from step 1 is still being metered in to the initially introduced aqueous alkaline solution.

* * * * *